United States Patent
Munting

(10) Patent No.: US 6,916,319 B2
(45) Date of Patent: Jul. 12, 2005

(54) INTERVERTEBRAL LINKING DEVICE WITH CONNECTING BAR FOR FIXING A LINKING ROD

(75) Inventor: Everard Munting, Biez (BE)

(73) Assignees: Scient'X, Guyancourt (FR); Bone & Joint Research S.A., Kayl (LU)

( * ) Notice: Subject to any disclaimer, the term of this patent is extended or adjusted under 35 U.S.C. 154(b) by 82 days.

(21) Appl. No.: 10/182,349

(22) PCT Filed: Jan. 26, 2001

(86) PCT No.: PCT/FR01/00259

§ 371 (c)(1),
(2), (4) Date: Nov. 5, 2002

(87) PCT Pub. No.: WO01/54597

PCT Pub. Date: Aug. 2, 2001

(65) Prior Publication Data

US 2003/0144665 A1 Jul. 31, 2003

(30) Foreign Application Priority Data

Jan. 27, 2000 (FR) .............................. 00 01071

(51) Int. Cl.$^7$ .............................. A61B 17/56
(52) U.S. Cl. .............................. 606/61
(58) Field of Search .............................. 606/61, 72, 60, 606/73

(56) References Cited

U.S. PATENT DOCUMENTS

| | | | | |
|---|---|---|---|---|
| 5,387,212 A | * | 2/1995 | Yuan et al. | 606/61 |
| 5,437,669 A | * | 8/1995 | Yuan et al. | 606/61 |
| 5,437,671 A | * | 8/1995 | Lozier et al. | 606/61 |
| 5,582,612 A | * | 12/1996 | Lin | 606/61 |
| 5,613,968 A | * | 3/1997 | Lin | 606/61 |
| 5,667,506 A | * | 9/1997 | Sutterlin | 606/61 |
| 5,702,392 A | * | 12/1997 | Wu et al. | 606/61 |

FOREIGN PATENT DOCUMENTS

FR    2781359    1/2000

* cited by examiner

*Primary Examiner*—Pedro Philogene
(74) *Attorney, Agent, or Firm*—Ladas & Parry LLP

(57) ABSTRACT

An intervertebral linking device of the type comprising bone anchoring elements to be interconnected by at least one intervertebral linking rod. The intervertebral linking device includes a the fixing system mounted on a connection bar the fixing system including at least one sliding displacement of the fixing system associated with a locking nut to lock said system in a fixed position. The connection bar is mounted on each anchoring element a guiding collar in rotation around an axis of the connection bar and locking the connection bar in a fixed specific position.

15 Claims, 5 Drawing Sheets

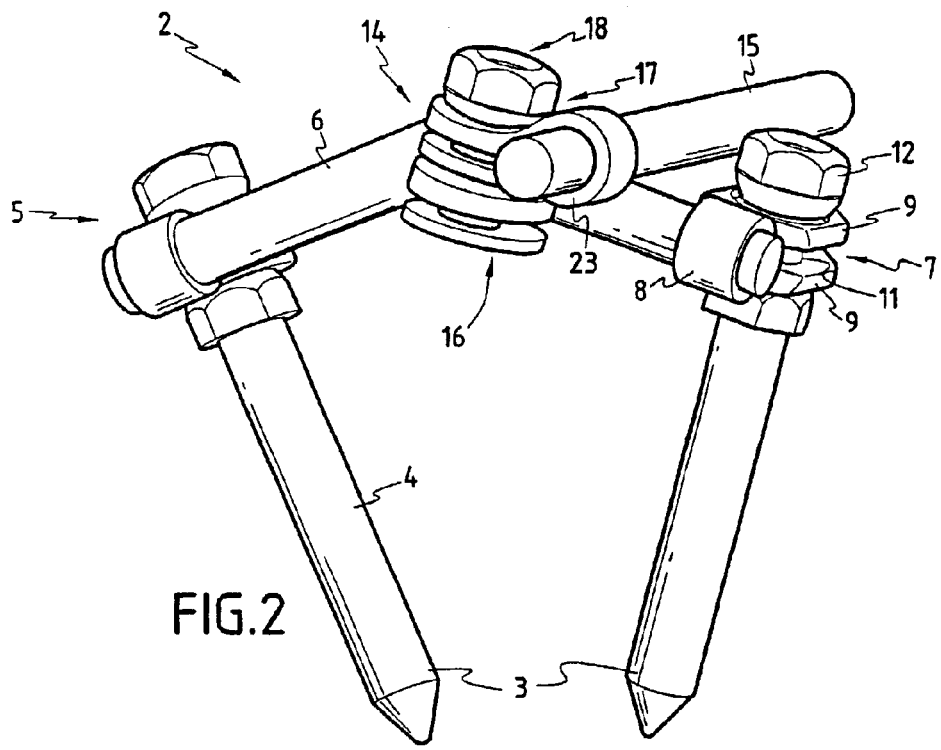
FIG.2
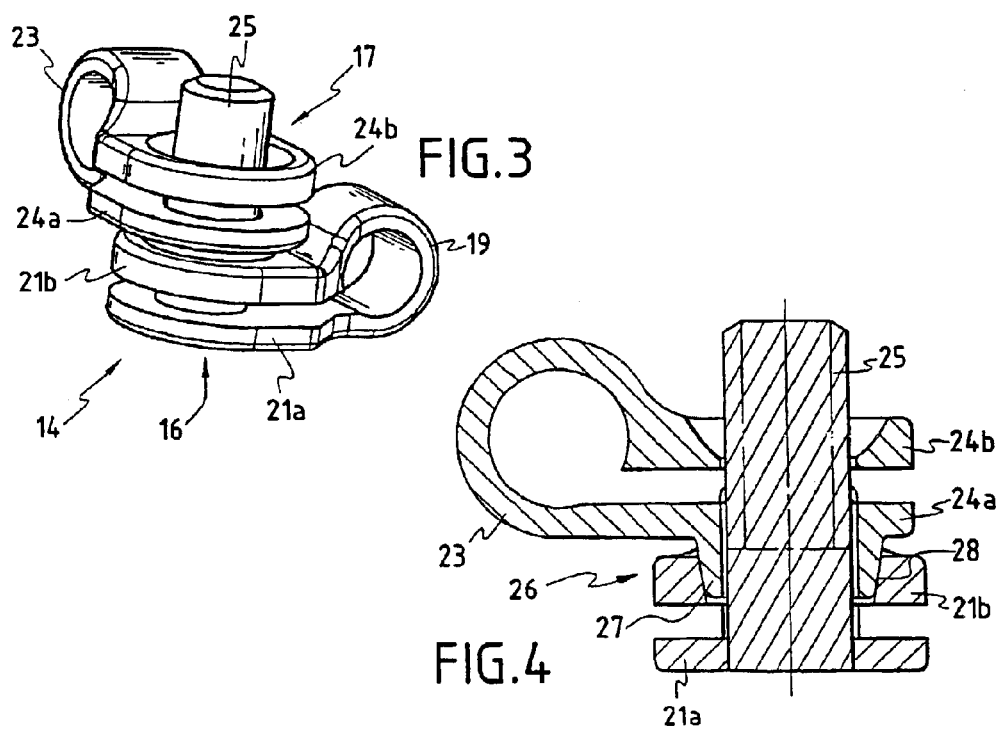
FIG.3
FIG.4

US 6,916,319 B2

INTERVERTEBRAL LINKING DEVICE WITH CONNECTING BAR FOR FIXING A LINKING ROD

FIELD OF THE INVENTION

The present invention generally concerns the technical field relating to osteosynthesis and relates to systems or devices ensuring an adapted intervertebral link for stabilizing or correcting deformations of the rachi and in particular scoliotic deformations.

BACKGROUND OF THE INVENTION

In the prior art, there are a large number of intervertebral linking devices. This type of device traditionally comprises bone anchoring elements, such as pedicular implantation screws or single or double vertebral hooks each equipped with a fixing head for a linking rod interconnecting said implants. The bone anchoring elements are distributed along the zone of the rachis to be treated to allow the mounting of two linking rods extending approximately parallel to each other by being placed on each side of the processi spinosus of the vertebrae. Sometimes a transversal crossing over between the linking rods is used to render the embodied construction more stable.

One of the difficulties for placing this intervertebral linking device concerns the connection between the intervertebral linking rods and the bone anchoring elements. This connection is rendered delicate owing in particular to the non-alignment inside the frontal plane of the bone anchoring elements of the difference in height between the bone anchoring elements and the angulation imposed by the anatomy of the rachis to be treated. These connection difficulties of these linking rods frequently reveal mechanical stresses which need to be added to those generated by an applied corrective or stabilizing action and which are likely to result in the pulling up, at least partially, of the bone anchoring elements, indeed a fracture of one of the main portions of this intervertebral linking device.

So as to try to overcome these drawbacks, the patent U.S. Pat. No. 5,437,671 describes an intervertebral linking device comprising a transversal connection bar secured to bone anchoring elements and equipped with two fixing systems for linking rods. Each fixing system of a linking rod is mounted on the connection bar by means of two hooks.

It is to be noted that this fixing system does not comprise any means to ensure it is locked in a fixed specific position along this connection bar. Furthermore, this document does not describe the mounting of the connection bar with a possibility of rotation around its axis and locking in a specific fixed position with respect to the anchoring screws.

Thus, this intervertebral linking device does not allow the linking rod to be adapted on the connection bar according to the three planes of the space. Moreover, this device does not make it possible to obtain a rigid structure between the linking rods and the transversal connection bars.

An examination of previous known solutions shows that there is a need to have available an intervertebral linking device designed in such a way with respect to the angular shift imposed by the rachis so as to facilitate the connection between the bone anchoring elements and an intervertebral linking rod whilst limiting the mechanical stresses imposed on the various main portions of such a linking device, especially by eliminating the stresses generated by the simple linking of the various anchoring elements whose alignment along the three planes of space can be faulty.

SUMMARY OF THE INVENTION

The object of the invention is to satisfy these requirement by offering an intervertebral linking device of the type comprising at least one fixing unit including:
  at least one bone anchoring element to be mounted on a vertebra,
  a connection bar secured to each anchoring element and having at least one curve,
  and a fixing system for at least one linking rod comprising means enabling it to be mounted in a specific position on the connection bar, these mounting means being equipped with fixing means for the linking rod so as to render integral said linking rod in a specific position with respect to the anchoring element with a view to ensuring a vertebral correction.

According to the invention:
  the means for mounting the fixing system on the connection bar are constituted by means ensuring at least one sliding of the fixing system and associated with means for locking said system in a fixed position.
  The connection bar is mounted on each anchoring element by means of guiding in rotation around its axis and locking in a fixed specific position.

BRIEF DESCRIPTION OF THE DRAWINGS

Other various characteristics appear in the following description with reference to the accompanying drawings which show by way of non-restrictive examples the embodiments and implementations of the object of the invention.

FIG. 2 is a perspective view showing a preferred embodiment example of a fixing unit according to the invention.

FIG. 3 is a perspective view of a fixing system forming part of the fixing unit shown on FIG. 2.

FIG. 4 is a front cutaway view of the fixing system shown on FIG. 3.

DETAILED DESCRIPTION OF THE PREFERRED EMBODIMENTS

Figure 1:
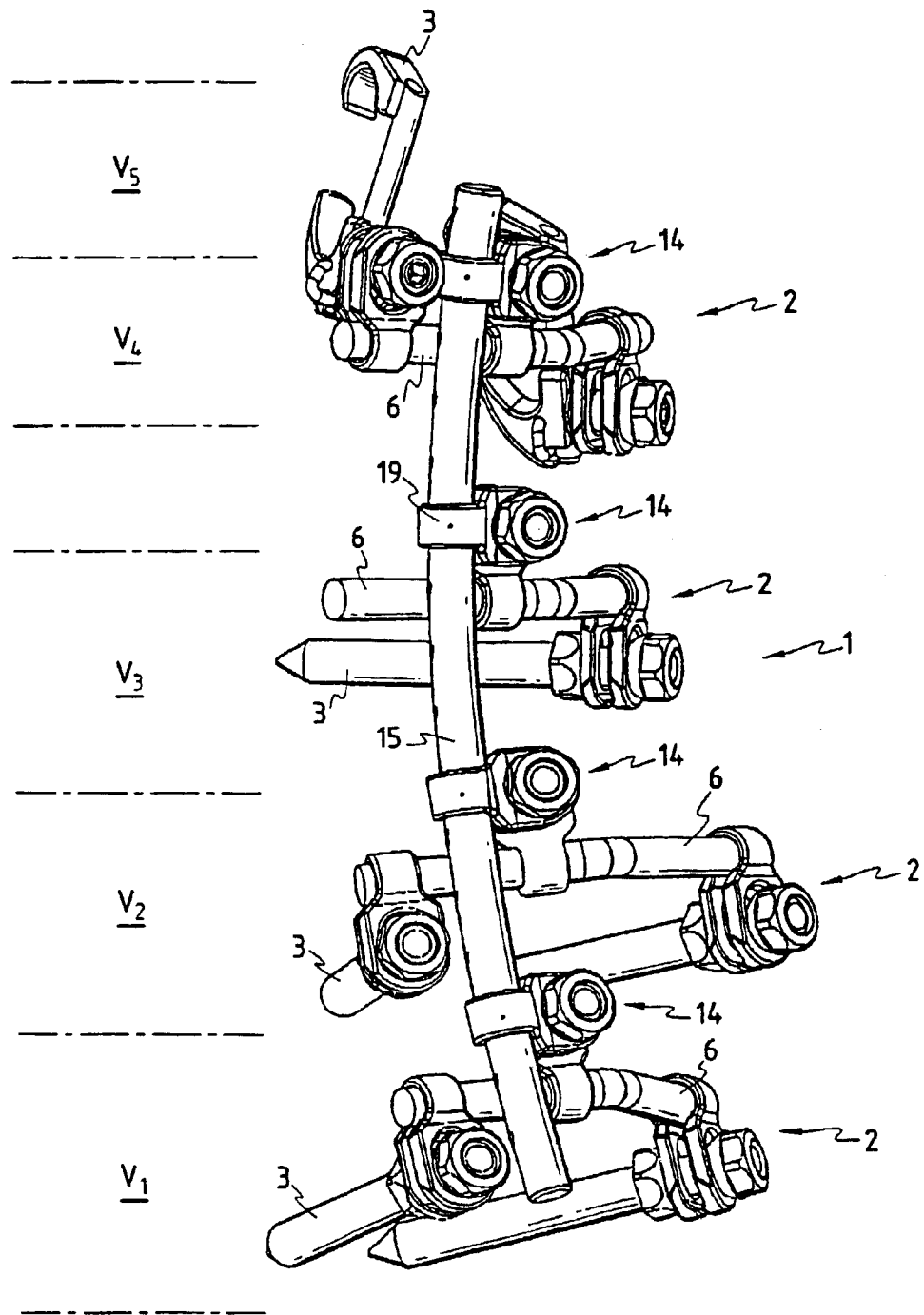
FIG. 1 is a perspective view showing an application example for an intervertebral linking device according to the invention.

As shown more specifically on FIG. 1, the object of the invention concerns an intervertebral linking device 1 comprising at least one and in the example shown four fixing units 2 conforming to the invention and adapted to be mounted on vertebrae shown diagrammatically by way of illustration by segments $V_1$ to $V_5$. Each fixing unit 2 comprises art least one and preferably two bone anchoring elements 3 intended to be mounted on two adjacent vertebrae or advantageously on a given vertebra. In the example shown on FIG. 2, each bone anchoring element 3 is constituted by a screw comprising a threaded anchoring rod 4 surmounted by a fixing head 5.

In accordance with the invention, each fixing unit 2 comprises a fixing bar 6 mounted on the anchoring element or elements (3) belonging to each fixing unit 2. According to the preferred embodiment variant in which a fixing unit 2 comprises a pair of anchoring elements 3, the anchoring elements 3 belonging to a one pair are interconnected by means of a connection bar 6, thus forming a bridge between the bone anchoring elements 3. This connection bar 6 is suitably mounted on the bone anchoring elements 3. In a preferred embodiment example, the connection bar has a circular cross section and is mounted on each bone anchoring element 3 by means of means 7 guiding the bar 6 in rotation around its axis and locking it in a fixed position. Preferably, the connection bar 6 has at least one curve whose function shall be given in more detail in the rest of the description.

In the illustrated embodiment, the guiding and locking means 7 are constituted by an open collar 8 defining a housing for a passage for an end portion of the connection bar 6. Each open collar 8 is extended by two branches 9 each designed in the form of ring to be inserted on a threaded extension 11 forming part of the fixing head 5 of the bone anchoring element 3. The extremity of the threaded extension 11 is intended to receive a nut 12 whose screwing makes it possible to close the collar resulting in locking of the connection bar 6 with respect to the bone anchoring elements 3.

According to another characteristic of the invention, the intervertebral linking device 1 comprises a fixing system 14 for at least one intervertebral linking rod 15. The fixing system 14 is mounted on the connection bar 6 so as to allow fixing of the linking rod 15 in a specific position with respect to the bone anchoring elements 3. According to an advantageous embodiment, the fixing system 14 comprises adapted means 16 to ensure it is mounted in a specific position along the length of the connection bar 6. These mounting means 16 are equipped with means 17 for fixing the linking rod 15.

In the embodiment example shown more specifically on FIGS. 3 and 4, the mounting means 16 of the fixing system 14 are constituted by means carrying out at least one sliding of this fixing system and associated with means 18 for locking said fixing the system 14 in a fixed position along the connection bar 6. Preferably, the mounting means 16 are designed to also make the fixing system 14 pivot around the axis of the connection bar 6. In the embodiment example shown on FIGS. 3 and 4, the mounting means 16 are constituted by means of an open collar 19, namely the first collar, for passage of the connection bar 6. Said first open collar 19 is extended on both sides by branches 21a, 21b, namely respectively lower and upper branches on which act as locking means 18 the tightening means, such as a nut in the example shown, making it possible to immobilize the first collar on the connection bar 6.

The means 17 for fixing the linking rod 15 are also constituted in a preferred embodiment example by means of a second collar 23 for passage of the linking rod 15. Said second open collar 23 is extended on both sides by the lower and upper branches 24a and 24b respectively on which the locking means act making it possible to lock or render integral the linking rod 15 with respect to the fixing system 14. According to one preferred embodiment characteristic, the means for locking the second collar 23 are similar to the means 18 for locking the first collar 19. These locking means 18 are constituted by a single element, namely a nut. To this effect, the first collar 19 comprises a lower branch 21a equipped with a threaded rod 25 traversing the upper branch 21b and designed in the form of ring. The second collar 23 also has lower 24a and upper 24b branches designed in the form of rings so as to enable them to be fixed on the threaded rod 25 which is covered by the tightening nut 18.

The means 17 for fixing the linking rod 15 are mounted on the mounting means 16 with a possibility of rotating around a rotation axis constituted by the threaded rod 25 extending for example approximately perpendicular to the connection bar 6. Preferably, the mounting means 16 and the fixing means 17 are fitted so as to comprise means 26 for ensuring an angular fastening between them. In the embodiment example shown, the means 26 are of the cone nesting type and formed by a cone 27 extending from the lower face of the branch 24a and cooperating with a truncated bore 28 delimiting the inside of the upper ring 21b. Tightening of the nut 18 results in the mutual driving in between the cone 27 and the truncated bore 28, thus ensuring an angular locking between the two collars 19, 23. Of course, it is possible to embody the angular adjustment means 26 differently, such as by means of rough portions made on the lower face of the ring 24a and on the upper face of the ring 21b.

The advantages of the intervertebral linking device 1 of the invention is directly specified in the preceding description. After the bone anchoring devices 3 are suitably implanted, the bone anchoring element or the two bone anchoring elements 3 of each fixing unit 2 is/are provided with a connection bar 6 equipped with its system 14 for fixing a linking rod 15. In the preferred case where the fixing unit 2 comprises a pair of anchoring elements 3, a connection bar 6 equipped with its fixing system 14 is thus mounted between the bone anchoring elements 3 of the pair. The anchoring elements 3 of each pair are installed on two adjacent vertebrae (for example $V_4$ and $V_5$) or preferably on a given vertebra (for example $V_1$ and $V_2$).

It is to be noted that the connection bar 6 is adapted so as to compensate height differences existing between the bone anchoring elements 3 of adjacent fixing units 2. This compensation can be obtained by the shape given to the connection bar 6 and/or by rotating allowing shifting inside the sagittal plane the height for fixing the linking rod 15. The connection bar 6 is also designed so as to be adapted to the vertebral anatomy and can thus have as shown in the example a concave curve directed towards the vertebra. This adjustment possibility facilitates the operations for mounting the linking rod 15 between the two adjacent fixing units insofar as the two points in the space can always be connected by a given straight line.

Moreover, each fixing device 14 is mounted fixed on the connection bar 6 in a selected position with respect to the bone anchoring elements 3. It is to be noted that the fixing device 14 can be mounted on the connection bar 6 between the bone anchoring elements 3 or outside the latter in a case where the connection bar 6 is extended on one side, thus enabling the linking rod 15 to be laterally fixed. This adjustment possibility inside the frontal plane makes it easier to fix the linking rod 15 on each fixing unit 2. The connection of the linking rod 15 is further facilitated by the possibility of carrying out an adjustment in the transversal plane crossing the axis of the rachis from the position of the receiving collar 23. The fixing system 14 for the linking rod 15 thus comprises a possibility for making a three-dimensional adjustment for facilitating the connection of the linking rod 15 whilst reducing the mechanical stresses imposed on the bone anchoring elements 3. In this respect, it is to be noted that fixing of the linking rod 15 on each connection 6 bar leads to distributing the forces. This distribution of forces is advantageously obtained for each unit 2 comprising two bone anchoring elements 3 on which the forces are distributed. The mechanical stresses imposed on each bone anchoring element 3 are therefore reduced with respect to the system of the prior art in which each bone anchoring element is submitted to the stresses imposed by a linking rod. The mechanical stresses applied to the bone anchoring elements 3 are limited to those generated mainly when the corrective or stabilizing action is carried out.

Moreover, it is to be noted that the intervertebral linking device 1 needs the use of a single linking rod 15. Of course, it is possible to carry out mounting on a connection bar 6 of a fixing unit 2, the extremities of the two linking rods 15 extending in the direction opposite each other. This linking device 1 can therefore be installed on separate or contiguous segments of the rachis.

It is to be noted that the fixing unit 2 of to the invention can be associated with other bone anchoring elements, such as hooks. Similarly, it is to be noted that the bone anchoring elements 3 can be constituted in a different way, such as for example by means of a single or double vertebral hook. Thus, as shown on FIG. 1, at least one, and in the example shown, two bone anchoring elements are each constituted by a double hook, such as the one described in the patent FR 2 763 236.

In the preceding description, the fixing device 14 is constituted mainly from two collars 19, 23 approximately identical forming a sort of brace. Of course, the fixing system 14 can be embodied differently.

Figure 5:
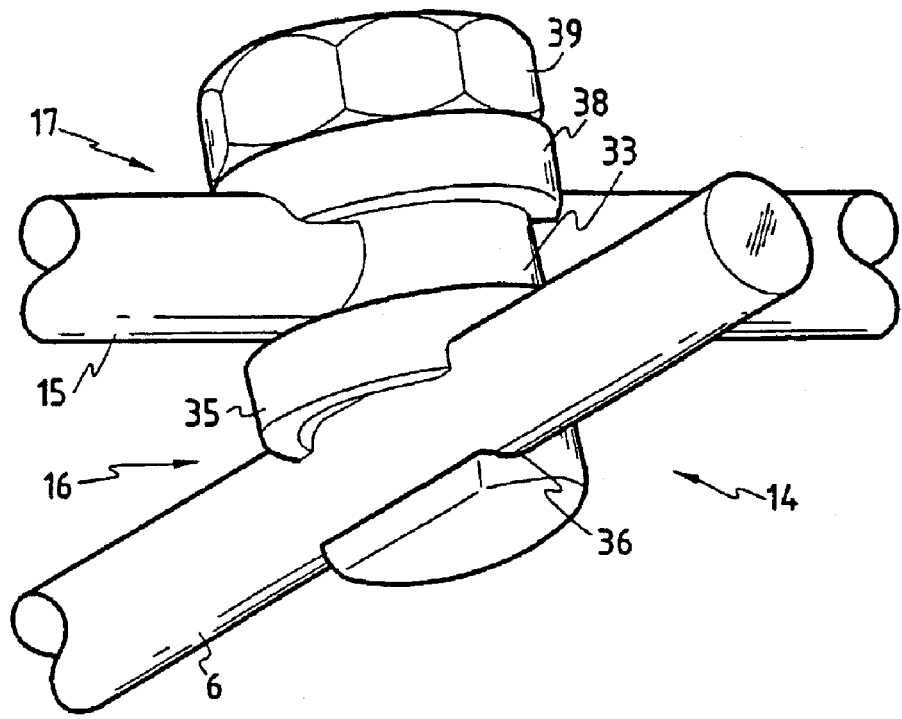
FIGS. 5 and 6 are respectively perspective and front cutaway views of another embodiment example of a fixing system according to the invention.
Figure 6:
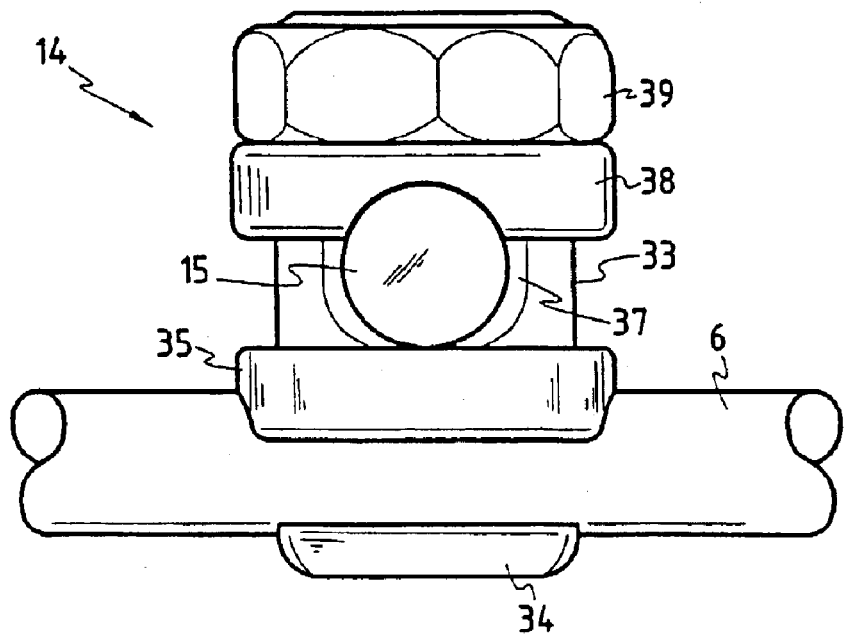

By way of example, FIGS. 5 and 6 describe a second embodiment variant of the fixing system 14 comprising mounting means 16 constituted by a support block 33 with the general shape of a cylinder and having at its lower extremity a jaw 34 delimiting with a support ring 35 a passage housing 36 for the connection bar 6. The support ring 35 is mounted free sliding on the support block 33. The support block 33 comprises a passage housing 37 for the linking rod 15. The passage housing 37 preferably has a passage cross section larger than the transversal cross section of the linking rod 15 so as to authorize an angular clearance adjustment. The fixing means 17 for the linking rod 15 are constituted by a nesting washer 38 mounted on the upper extremity of the support block 33 so that the linking rod 15 is tightened between the nesting washer 38 and-the support ring 35. The extremity-of-the support block 33 is threaded so as to receive a nut 39 acting on the nesting washer 38 so as to ensure by tightening the immobilization of the linking rod 15 on the fixing system 14 and of said system 14 on the connection bar 6.

Figure 7:
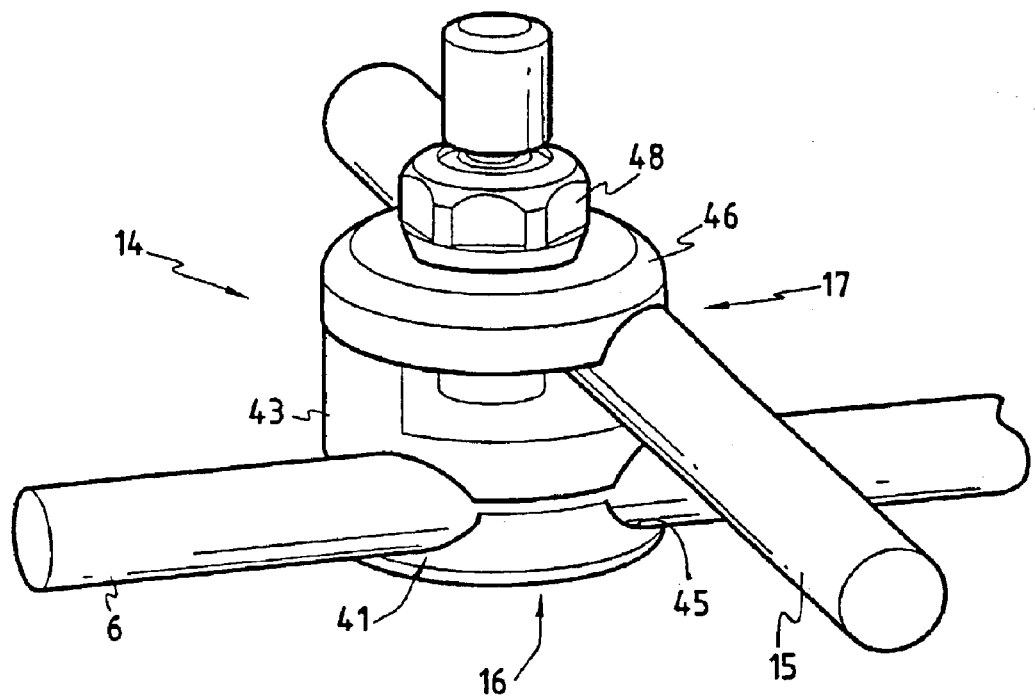
FIGS. 7 and 8 are respectively perspective and front cutaway views of another embodiment example of a fixing system according to the invention.
Figure 8:
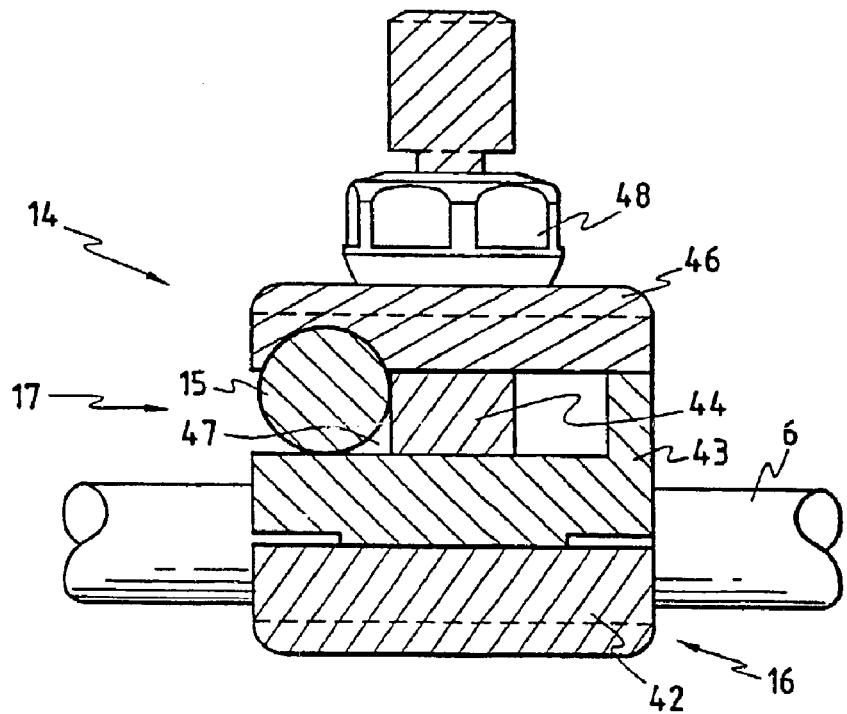

FIGS. 7 and 8 describe a third embodiment variant of a fixing system 14 comprising mounting means 16 constituted by a stirrup 41 formed between a body 42 and an intermediate boat-shaped element 43. The body 42 appears in the form of a disk surmounted by an extension 44 on which the intermediate boat-shaped element 43 is mounted in a superposition position. The disk 42 and the intermediate boat-shaped element 43 are shaped so as to delimit between them a passage housing 45 for the connection bar 6.

The fixing means 17 are constituted by a support boat-shaped element 46 mounted on the extension 44 of the body and nesting the intermediate boat-shaped element 43 by delimiting between them a passage housing 47 for the linking rod 15. As shown by the drawings, the passage housing 47 is offset with respect to the axis of the extension 44. The support boat-shaped element 46 is surmounted by a nut 48 screwed on a threading embodied by the extension 44 of the body. The tightening of the nut 48 results in locking of the fixing system 14 in the connection bar 6 and of the linking rod 15 on the fixing system 14.

Figure 9:
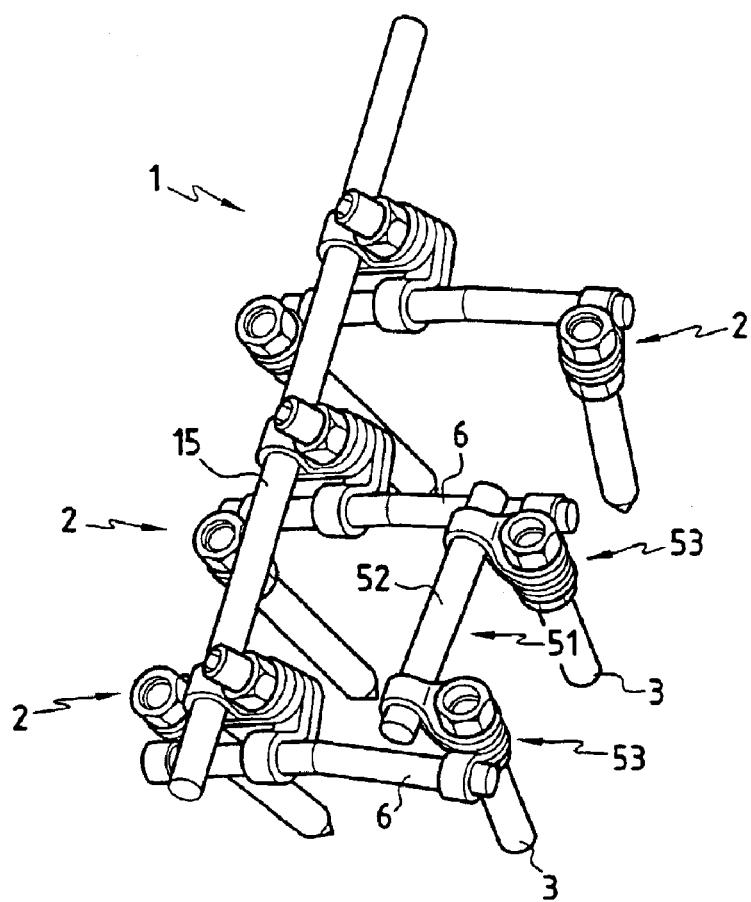
FIG. 9 is a perspective view showing an embodiment variant of the linking device of the invention.
Figure 10:
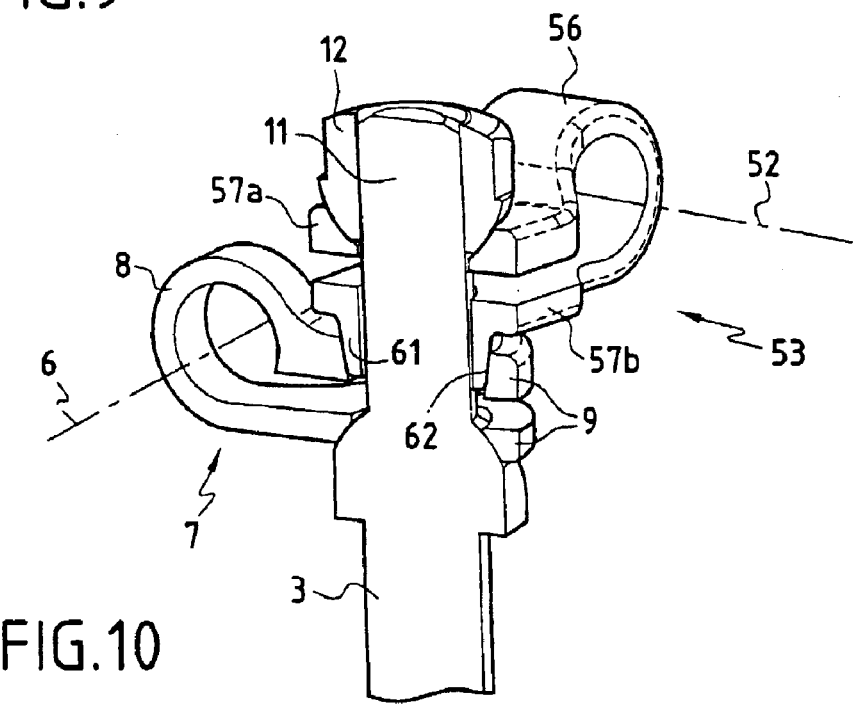
FIG. 10 is a partially pulled up perspective view showing characteristic details of the variant shown on FIG. 9.

FIGS. 9 and 10 show a variant of the intervertebral linking device 1 of the invention for increasing the mechanical resistance between at least two fixing units 2 with the aid of at least one bracing system 51. In the example shown, the device 1 comprises a bracing system 51 between two adjacent fixing units 2. The bracing system 51 ensures a link between the connection bars 6 of the fixing units 2. The bracing system 51 comprises an additional linking rod 52 equipped with means 53 for mounting in a fixed position on two anchoring elements 3 situated opposite and belonging to the two fixing units 2.

The mounting means 53 preferably are able to rotate around a spin axis merged with the axis of the anchoring element 3. As shown on FIG. 10, the means 53 for mounting the additional linking rod 52 on each anchoring element 3 are constituted by an open passage collar 56 for the additional linking rod 52. Each open collar 56 is extended by two branches, respectively an upper branch 57A and lower branch 57b formed into the shape of a ring intended to be inserted on the threaded extension 11 of the anchoring element 3 above the branches 9 of the receiving collar 8 of the connection bar 6. The mounting means 53 and the guiding and locking means 7 are preferably fitted so as to comprise means ensuring an angular-adjustment-between them. These means are of the conical nesting type and are formed by a cone 61 extending from the lower face of the lower branch 57b of the collar 56 and cooperate with a truncated bore 62 delimiting the inside of the upper ring 9 of the collar 8. The tightening of the nut 12 on the extremity of the threaded extension 11 results in a mutual driving in between the cone 61 and the truncated bore 62 ensuring an angular locking between the two collars 8, 56 and a locking of the connection bar 6 and the additional linking rod 52 respectively by the collars 8, 56.

This bracing system 51 is able to ensure a link between two connection bars 6 and able to adjust the orientation of the additional linking rod 52 with respect to the direction passing through the two anchoring screws supporting the mounting collars 56. The bracing system 51 is preferably mounted on the anchoring screws 3 which are the most distant from the linking rod 15. The linking rod 15 and the additional linking rod 52, as well as the connections bars 6, constitute a sort of stiffening frame for keeping the structure created in a specific fixed position.

In the example shown above, the additional linking rod 52 is mounted on two fixing units 2. Of course, the additional linking rod 52 can be mounted on a large number of fixing units 2. Similarly, it is also possible to mount the additional linking rod 52 on fixing units which are not close to one another.

What is claimed is:

1. An intervertebral linking device comprising at least one fixing unit including:
   at least one bone anchoring element to be mounted on a given vertebra,
   a connection bar secured to each anchoring element and having at least one curve, and
   a fixing system for at least one linking rod and comprising means to mount said fixing system in a specific position on the connection bar, these mounting means being equipped with fixing means for the linking rod so as to ensure said linking rod is rendered integral in a specific position with respect to the anchoring element ensuring a vertebral correction, wherein;

the mounting means of the fixing system on the connection bar including at feast one sliding element of the fixing system associated with means for locking said system in a fixed position, the connection bar being mounted on each anchoring element by a guiding means for guiding the connection bar in rotation around an axis of the connection bar and locking the connection bar in a specific fixed position;

wherein the mounting means of the fixing system on the connection bar and the fixing means for the linking rod include a first open collar and second open collar for passing respectively from the connection bar and from the linking rod, each open collar being fitted with locking means able to ensure immobilization of the fixing system on the connection bar and of the linking rod with respect to the fixing system.

2. Device according to claim 1, further comprising at least one fixing unit including a pair of bone anchoring elements intended to be mounted on a given vertebra or on two adjacent vertebrae, the connection bar being fixed between a pair of anchoring elements.

3. Device according to claim 1, wherein the fixing means for the linking rod are mounted on the mounting means to rotate around a spin axis.

4. Device according to claim 3, wherein the mounting means and the fixing means are fitted so as to comprise angular adjustment means ensuring a locking between the mounting means and the fixing means.

5. Device according to claim 1, wherein the mounting means of the fixing system on the connection bar includes means for pivoting the fixing system around the axis of the connection bar.

6. Device according to claim 1, wherein the locking means for the collars are made of a single piece.

7. Device according to claim 6, wherein the locking means for the collars include a nut cooperating with a threaded rod extending from a branch of the first collar, whereas the other branch of said collar is traversed by the threaded rod on which rings are fixed extending from the second collar and intended to be covered by the nut to ensure the locking of the connection bar and the linking rod.

8. Device according to claim 1, wherein the mounting means of the fixing system on the connection bar and the fixing means for the linking rod include a support block having a jaw delimiting with a support ring a passage housing for the connection bar, the support ring being mounted in free displacement on the support block and on which the linking rod is intended to come into support, said linking rod traversing the support block and inserted between said ring and a covered washer intended to ensure with the aid of a nut the locking by tightening of the linking rod on the fixing system and of said system on the connection bar.

9. Device according to claim 1, wherein:

the mounting means of the fixing system on the connection bar include a stirrup formed between a body and an intermediate boat-shaped element mounted on the body in a superposition position and delimiting between them a passage housing for the connection bar, and the fixing means for the linking rod include a support boat-shaped element mounted on the body and covering the intermediate boat-shaped element by delimiting between them a passage housing for the linking rod, the support boat-shaped element being surmounted by a nut screwed onto a threaded extension exhibited by the body allowing the locking of the fixing system on the connection bar and of the linking rod on the fixing system.

10. Device according to claim 1, wherein the means for guiding and locking in rotation of the connection bar includes an open passage collar for the connection bar extended by two branches each shaped in the form of a ring intended to be inserted on a threaded extension forming part of the fixing head of an anchoring element and intended to receive a locking nut.

11. Device according to claim 1, further comprising as a bone anchoring element, a pedicular screw or a single or double hook.

12. Device according to one of claims 1 to 11, further comprising a set of fixing units each mounted on at least one given vertebra and interconnected by means of at least one linking rod.

13. Device according to claim 12, further comprising for at least two fixing units mounted on two vertebrae at least one bracing system between the connection bars belonging to said fixing units, each bracing system comprising an additional linking rod provided with means for mounting in a fixed position on the anchoring elements situated opposite and belonging to the fixing units.

14. Device according to claim 13, wherein the means for mounting the additional linking rod in a fixed position on the anchoring elements are able to rotate around a spin axis merged with the axis of the anchoring element.

15. Device according to claim 14, wherein the means for mounting the additional linking rod in a fixed position on each anchoring element are constituted by an open passage collar for the additional linking rod extended by two branches shaped in the form of a ring intended to be inserted on a threaded extension forming part of the fixing head of an anchoring element and also passing into the branches of the passage collar for the connection bar, the threaded extension being intended to receive a locking nut.

* * * * *